(12) United States Patent
Chambers et al.

(10) Patent No.: US 9,102,574 B1
(45) Date of Patent: Aug. 11, 2015

(54) WORM COMPOSTING MACHINE

(75) Inventors: Jack L. Chambers, Sonoma, CA (US);
Thomas R. Craig, Sonoma, CA (US);
David Zappetini, San Rafael, CA (US)

(73) Assignee: Jack L. Chambers, Sonoma, CA (US)

( * ) Notice: Subject to any disclaimer, the term of this patent is extended or adjusted under 35 U.S.C. 154(b) by 712 days.

(21) Appl. No.: 13/356,524

(22) Filed: Jan. 23, 2012

(51) Int. Cl.
| | |
|---|---|
| *C12M 1/00* | (2006.01) |
| *C05F 17/02* | (2006.01) |
| *B01F 13/00* | (2006.01) |
| C12M 1/06 | (2006.01) |
| B01F 3/12 | (2006.01) |
| C05F 17/00 | (2006.01) |
| B01F 7/00 | (2006.01) |

(52) U.S. Cl.
CPC ......... *C05F 17/0205* (2013.01); *B01F 13/0035* (2013.01); *C05F 17/0235* (2013.01); *B01F 3/1221* (2013.01); *B01F 7/0025* (2013.01); *B01F 13/0015* (2013.01); *B01F 13/0037* (2013.01); *B01F 2215/0054* (2013.01); *C05F 17/0063* (2013.01); *C05F 17/0241* (2013.01); *C05F 17/0258* (2013.01); *C12M 27/02* (2013.01)

(58) Field of Classification Search
CPC ............. C05F 17/0241; C05F 17/0258; C05F 17/0235; C05F 3/06; C05F 17/00; C05F 17/0009; C05F 17/0205; C05F 17/0247; C05F 17/02; C05F 17/0027; A01K 1/0155; A01K 67/0332; A01K 1/01; A01K 1/10; A01K 31/007; A01K 5/0266; C05D 9/00; C05D 1/00; A01C 3/026; A47L 13/00; B65D 2565/382; A01G 31/02; A01G 1/044; B22C 5/0486; B01F 13/0035; B01F 13/0037; B01F 13/00; B01F 13/0015; B01F 13/0047; B01F 2215/0054; B01F 3/1221; B01F 7/00358; B01F 13/0013; B01F 7/0025; B01F 7/04; B01F 7/1605; Y10S 241/10; Y10S 241/38; Y10S 366/607; A01J 25/005; A61H 15/0092; A61H 2015/0064; A61H 23/0218; B02C 18/0076; B02C 18/0084; B02C 18/26; C12M 27/02; C21B 7/10; C22B 7/001; C22B 7/005; Y10T 403/32426; Y10T 74/18344
USPC ..................... 435/289.1, 290.1, 290.2, 290.3; 366/345, 346, 332
See application file for complete search history.

(56) References Cited

U.S. PATENT DOCUMENTS

| | | | | |
|---|---|---|---|---|
| 5,758,462 | A * | 6/1998 | Finn | ............................. 52/302.1 |
| 2010/0015693 | A1 * | 1/2010 | Lewis et al. | ............... 435/290.1 |

* cited by examiner

*Primary Examiner* — Michael Marcheschi
*Assistant Examiner* — Shanta G Doe
(74) *Attorney, Agent, or Firm* — Thomas M. Freiburger

(57) ABSTRACT

A composting machine, particularly for vermicompost, is elongated in shape. Grates with openings are laid into a frame of the machine, onto cross beams which correctly locate the grates to be closely adjacent to one another except along a longitudinal center line of the machine, where the spaced-apart grates form a guiding channel through the length of the machine. Within this travels a downwardly extending keel of a carriage that is moved through the length of the machine when a bottom layer of finished compost is to be harvested from the bottom of the mass of compost material. To the carriage is attached a cutting blade extending the width of the machine, driven by longitudinal tension lines under the control of a driving motor. A tensioner maintains tension in the cable.

15 Claims, 13 Drawing Sheets

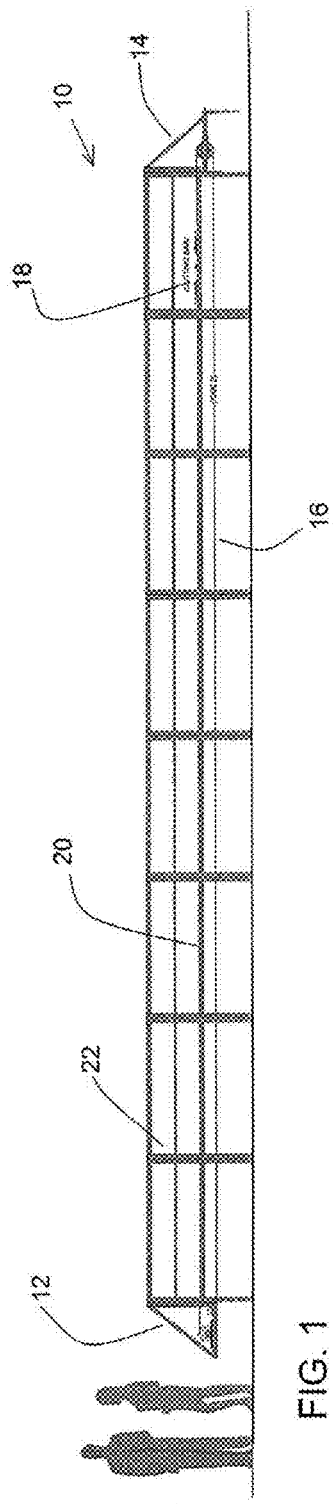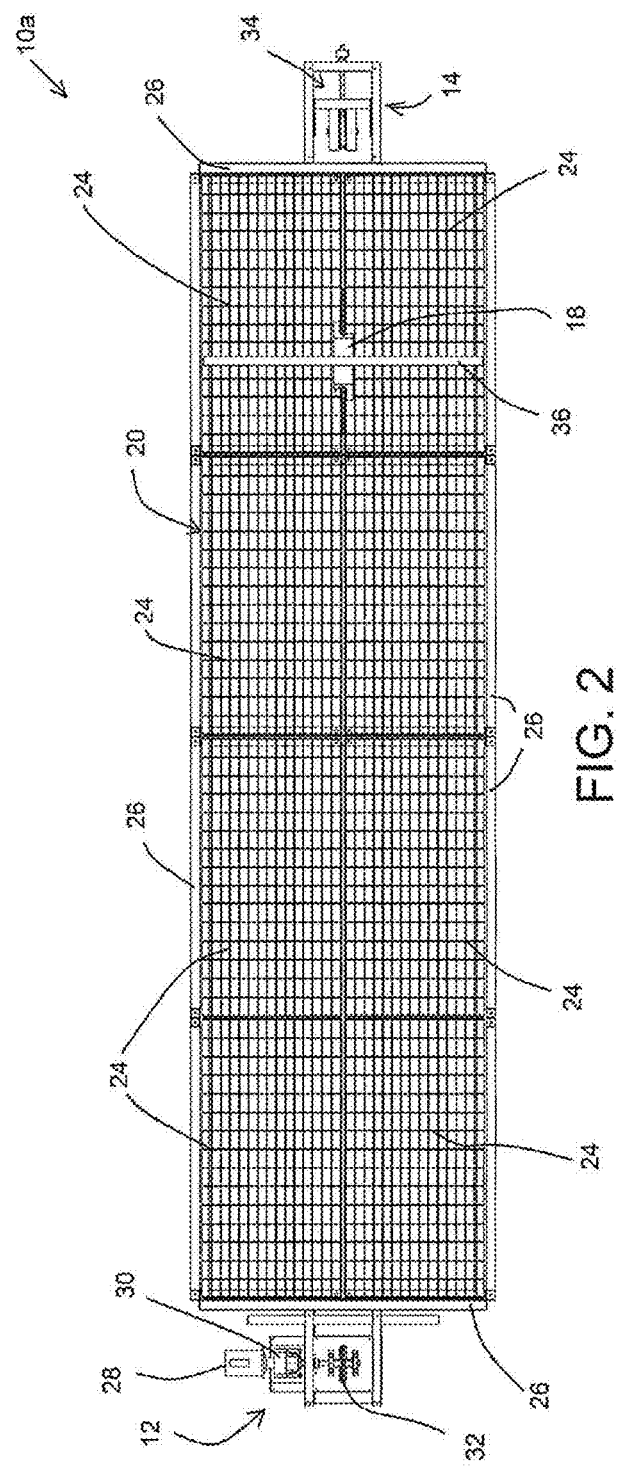

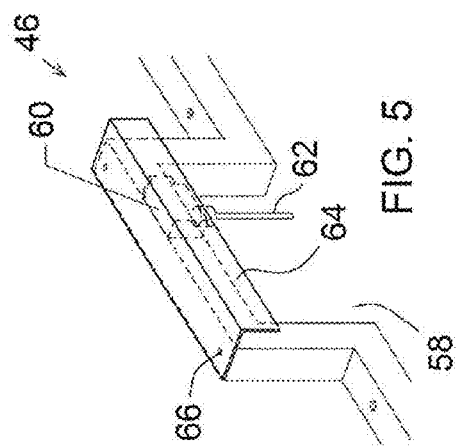
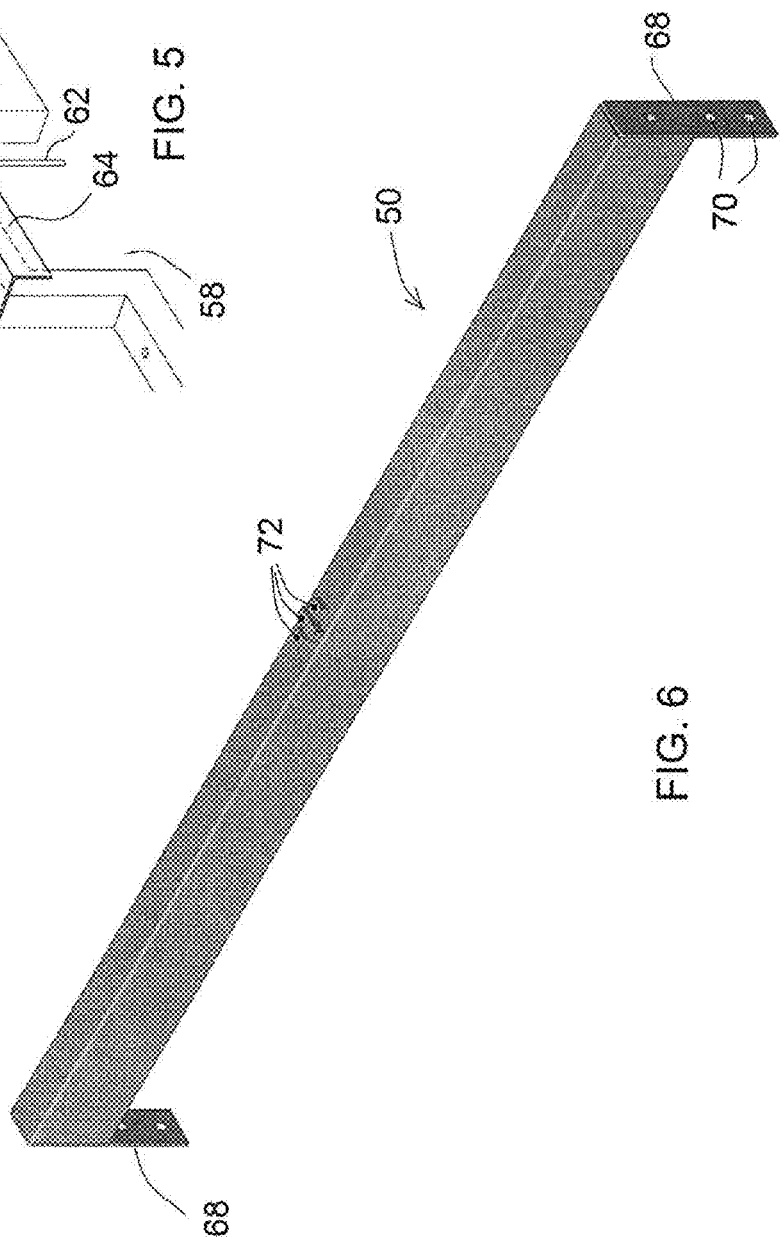

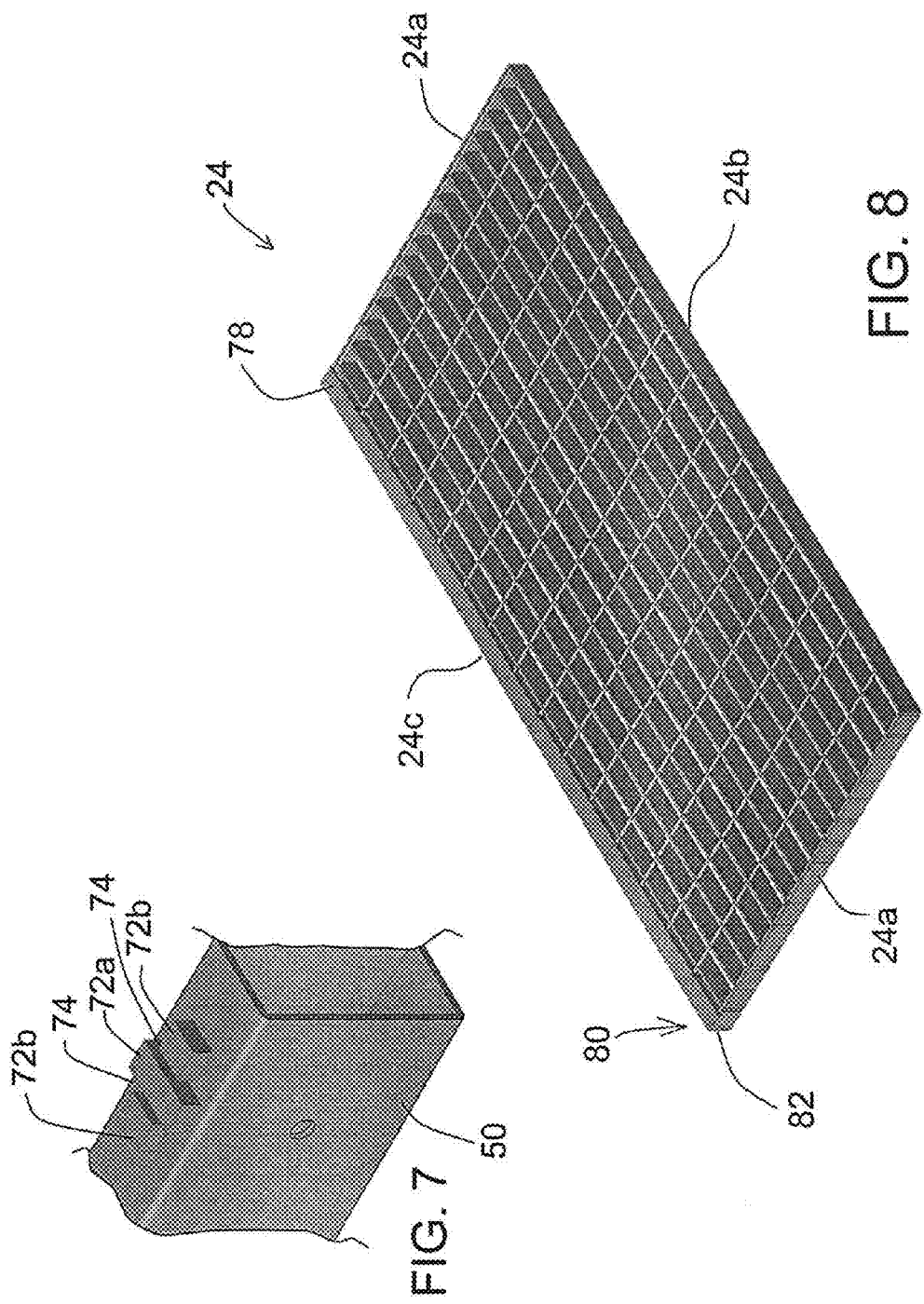

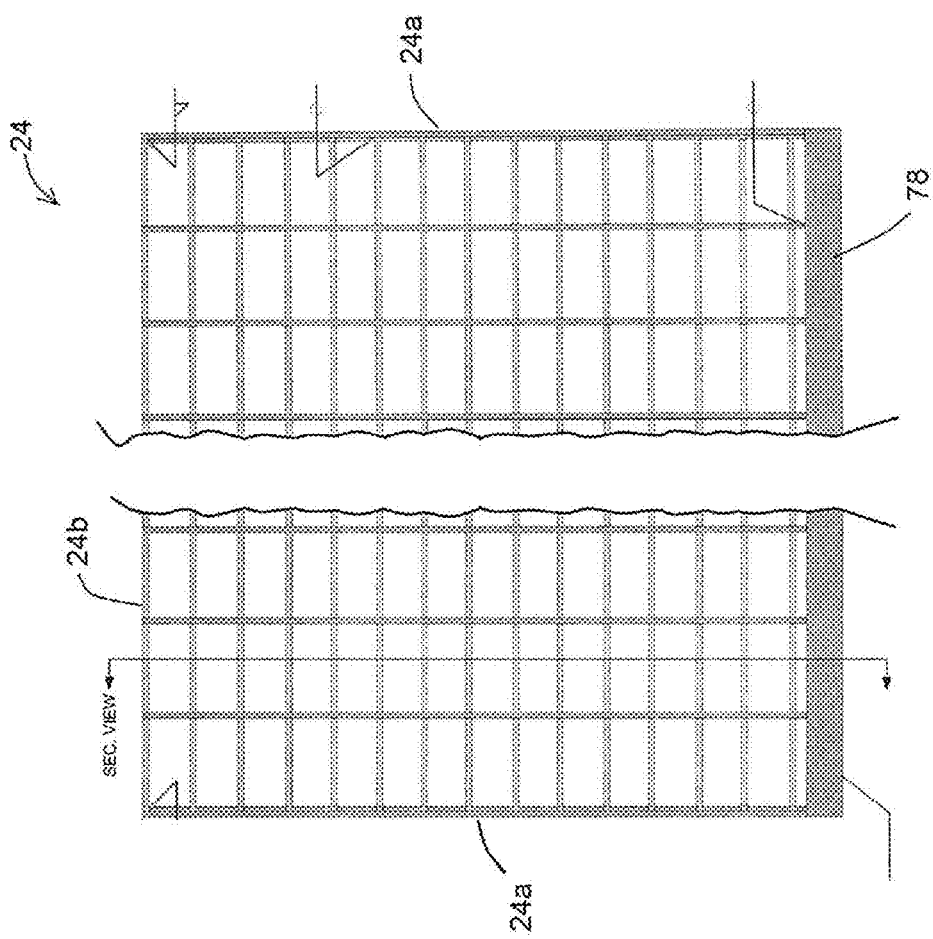

WORM COMPOSTING MACHINE

BACKGROUND OF THE INVENTION

The invention concerns production of vermicompost, the special compost produced by composting a material such as manure, with worms living within the compost and leaving their casts. In particular, the invention is directed to a composting machine which is elongated in length and which enables periodic feeding of new composting material to the top of a compost pile within the machine, and harvesting of finished compost from the bottom of the compost pile, through an open-grate floor. The invention also encompasses a method of composting involving the machine.

Vermicompost is well known as an excellent soil for plants and an amendment for crop soils. A "compost tea" is often made by brewing the vermicompost with water, for use in amending soils. In addition, the finished vermicompost can be added to any compost, even at about 10% to 20% vermicompost, and this is known greatly to improve plant growth. The casts from the worms is known to be many times more microbially active than what is normally found in a compost pile, sometimes said to be approximately 1000 times as microbially active.

Machines for vermicomposting of materials, such as manure, have been known. The machines or compost stands have taken many forms, and some have had a form of cutting blade near the bottom of the compost pile, for harvesting a layer of finished compost. Fresh material is added to the top of the compost pile, and the finished compost is harvested on a regular basis.

None of the composting machines and arrangements of the prior art have had the advantageous features of the invention described below.

SUMMARY OF THE INVENTION

The invention provides a composting container and machine, particularly for vermicomposting, of far more efficient design and operation than existed in the prior art. The composting machine is elongated in shape, e.g. twenty feet to forty feet long or greater, and with a narrow width that can be about five feet. Grates with openings that may be about two inches by four inches are laid into a frame of the machine, onto cross beams which correctly locate the grates to be closely adjacent to one another except along a longitudinal center line of the machine, where a guiding channel is formed through the length of the machine. Within this travels a bottom keel of a carriage that is moved through the length of the machine when a bottom layer of finished compost is to be harvested from the bottom of the mass of compost material. To the carriage is attached a cutting blade extending through the width of the machine, driven by longitudinal tension lines under the control of a driving motor. A tensioner maintains tension in the cable.

An important feature of the invention is the limited length of the keel of the moving carriage. Preferably it is no greater than fifteen inches in length, and more preferably twelve inches or less in length.

The well defined and consistent channel through which the keel is movable allows smooth and reliable travel of the keel with only this limited length. A keel of only one foot length will extend beyond the end of the compost pile (and the end wall of the machine) by only about five inches. This is important in limiting the necessary size of the end extensions on the machine, where the motor, gearbox, return pulley and pulley tensioner are located.

The cutting blade rides above the surface of the floor defined by the grates, and the distance above the grates may be approximately ¾ inch, although this could vary. The transverse ends of the cutting blade preferably are not fully cantilevered from the carriage, but instead, each end includes a "pontoon" secured to the end and extending downwardly to rest on a skid plate formed at the outer edges of the grids, so that these pontoons can slide on the skid plates to maintain the desired positioning of the cutting blade above the grates.

Another important feature is the means by which the grates, which are liftable out of the machine, are correctly located in the frame so as to be closely abutted but defining the uniformly shaped longitudinal channel for the sliding movement of the keel. The cross beams of the frame have upwardly extending nubs or protrusions that enter into openings of the grids and correctly locate all of the grates.

In a preferred embodiment of the invention, the motor and gearbox are on an end extension at one end of the machine, while a tensioner is on an extension at the opposite end of the machine. The tension cable rides around pulleys, the cable being secured to the carriage at both front and back, and extending over a drive pulley near the motor and a tensioning pulley at the opposite end, the loop of the cable being completed at the bottom of the machine, below the center line.

For more efficient cutting, the cutting blade in a preferred embodiment has a cross sectional shape generally convexly curved at the upper side, and preferably generally flat or planar at the lower side. This shape minimizes resistance and promotes efficient cutting.

Accordingly, it is an object of the invention to provide for efficient composting and harvesting of compost material in an elongated and partially automated machine. The invention also encompasses the method of composting and obtaining a finished vermicompost product using the machine, in combination with other steps. These and other objects, advantages and features of the invention will be apparent from the following description of a preferred embodiment, considered along with the accompanying drawings.

DESCRIPTION OF THE DRAWINGS

FIG. 1 is a schematic side elevational view showing an embodiment of a composting machine of the invention, in approximately forty foot length.

FIG. 2 is a top plan view showing the machine.

FIG. 5 is a detail view in perspective, showing a portion of an end frame of the machine.

FIG. 6 is a perspective view showing a cross beam which is part of the frame of the machine.

FIG. 7 is a detail view showing a portion of the cross beam of FIG. 6 and indicating locator stops or protrusions.

FIG. 8 is a perspective view showing one of the grates to be fitted into the frame and comprising a part of the machine.

FIG. 9 is a plan view indicating construction of a grate.

DESCRIPTION OF PREFERRED EMBODIMENTS

Figure 3:
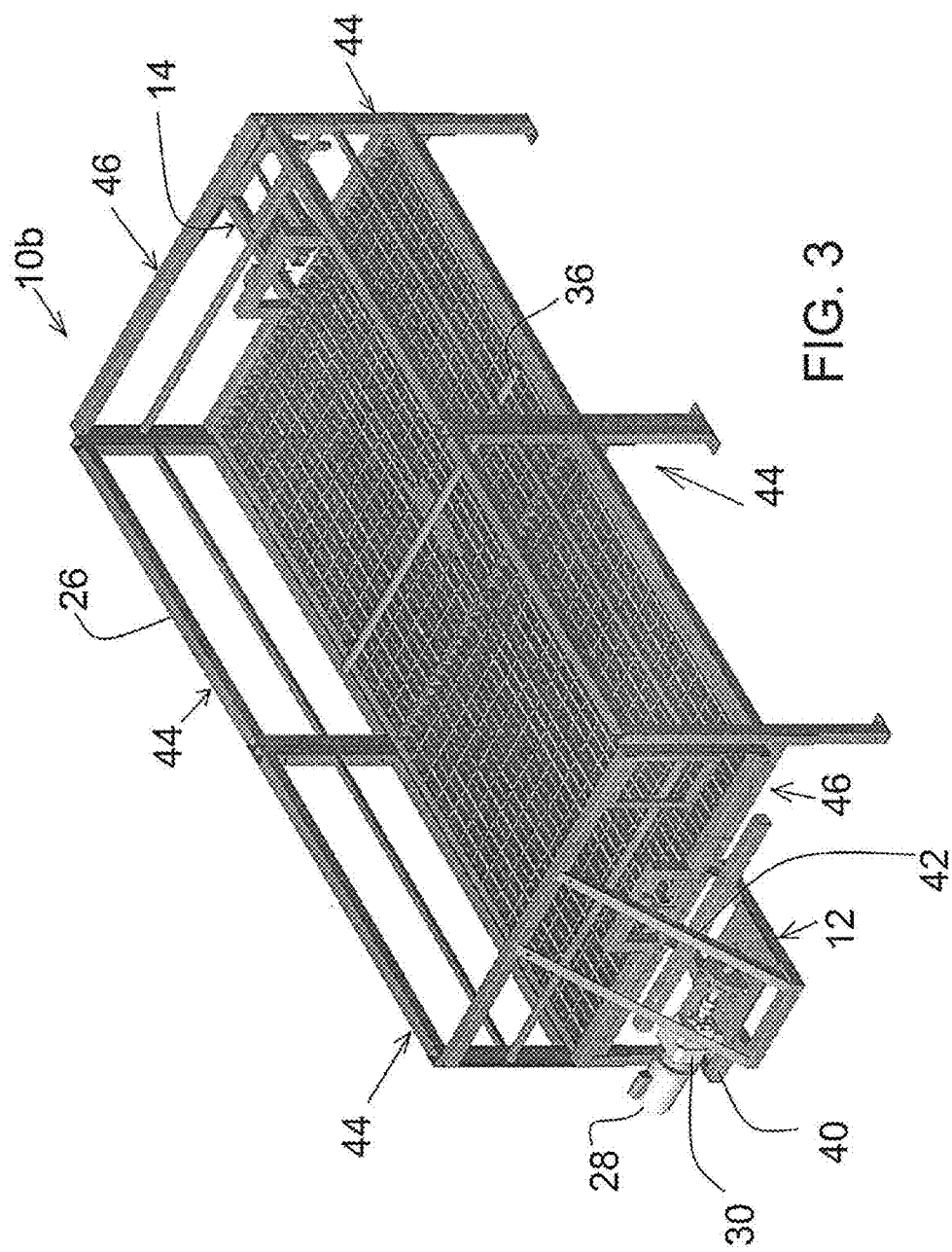
FIG. 3 is a perspective schematic view showing a shortened version of the machine.

FIG. 1 schematically shows an example of the machine 10 of the invention in side elevation view. The indicated machine 10 has a length of approximately forty feet and a height which may be about four feet, or more preferably about 44 inches, or a range of about 40 inches to 48 inches. The machine, which can be in greater or lesser lengths (preferably at least about fifteen feet), has a motor end extension 12 at one end and a tensioner end extension 14 at the opposite end. A tension cable or line is seen at 16, driving a cutting bar/carriage assembly 18, barely visible in this view. A floor of the composting space within the machine is seen at 20, formed by laid-in grates as explained below, the compost being plowed on this floor and contained within walls extending up around the periphery of the floor, a portion of a side wall being seen at 22.

FIG. 2 shows the machine in plan view, in this case showing a much shorter machine 10a. This machine may be about twenty feet in length. In this version of the machine the composting floor 20 is formed of eight grates 24, each laid into a frame, peripheral rails 26 of which can be seen in this plan view. End extensions are secured to the frame and shown at 12 and 14 as also seen in FIG. 1. A motor 28 and gearbox 30 are seen mounted on the extension 12, for rotating a driving pulley 32, and at the opposite end of the machine, the frame extension 14 supports a tensioner assembly 34, explained further below. FIG. 2 also shows schematically a cutting blade 36 of the carriage assembly 18, the blade extending essentially through the width of the cutting floor 20 and being spaced above the grates a prescribed distance. The carriage assembly 18 travels along a longitudinal central trough or channel 38 formed between the grates, as further explained below.

FIG. 3 shows a foreshortened version of the composting machine 10b in perspective. The machine is foreshortened for purposes of illustration, shown with only four grates 24, the length defined by two grates. If the grates are about five feet long, as is preferred in one embodiment, the form of machine shown in FIG. 3 would not be likely, although it is possible. More efficient generation of finished compost is achieved with a machine of twenty feet, forty feet or greater length.

The motor 28 and gearbox 30 are secured together and mounted on a platform 40 of the frame end extension 12. A motor pulley cover is shown at 42. The end extension may be supported as shown, with the platform secured to the end of the machine frame and supported by angled struts 42. The frame extension 14 at the opposite end can be supported similarly.

What is referred to as the frame or support frame is comprised of a series of side frame members 44 that secured together to bind the length of the machine, and end frame members 46 at opposing ends. These are secured together, preferably by bolting as discussed further below, and they support cross beams 50 extending transversely in the frame, the cross beam being seen in the exploded view of FIG. 4. The cross beams are parallel to one another and at fixed spacings, secured to the frame members 44, again preferably by bolting. These cross beams are positioned specifically to support and properly locate the series of grids at 24 that rest upon them. Each end 24a of a grate rests on a cross beam. The cross beams 50 where the ends of grates abut together can be doubled, as is indicated in FIG. 4, or a wider, special cross beam could be provided at these abutting joints so that the grids at both sides of a joint rest on the same cross beam member.

Figure 4:
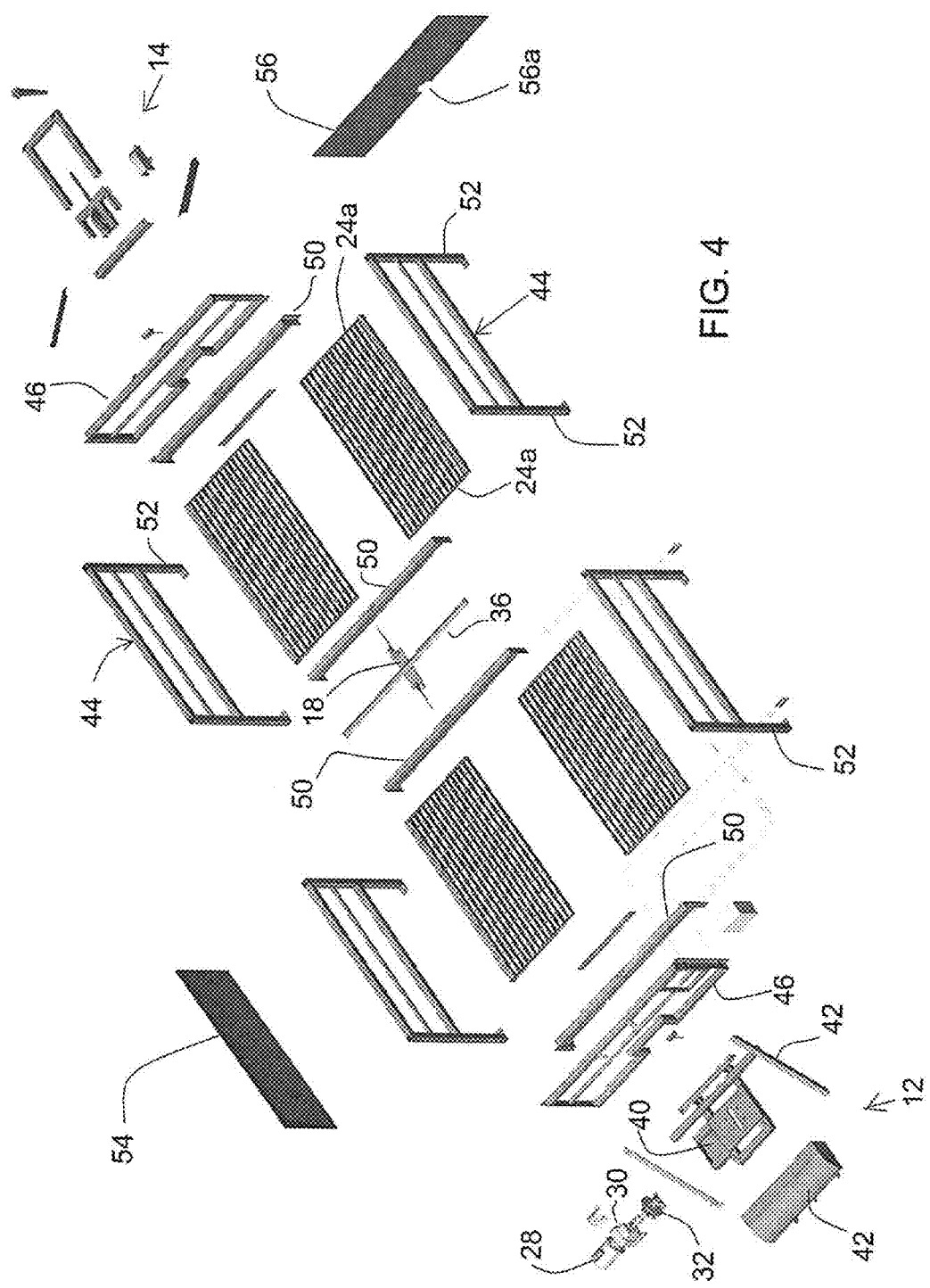
FIG. 4 is an exploded view indicating the components to be assembled for the shortened version of the machine shown in FIG. 3.

FIGS. 3 and 4 also show that the end frame panels 46, of which there are two, preferably are without legs. They are simply connected into the side frame panels 44, which are supported by panel legs 52.

The side and end frame members or panels 44 and 46 are open frames, and the foreshortened example of the machine 10b in FIG. 3 is shown in this way. These frame members must of course be closed to retain compost, and this preferably is accomplished with solid wall or panel members 54, 56 that are secured to each of the side and end frame members 44 and 46. They can be of relatively thin corrugated material, metal or plastic. These wall pieces are exemplified by one of each in the exploded view of FIG. 4, with the walls being about 24 inches high above the composting floor. Note that in the end wall pieces 56 a notch 56a is provided at the bottom center, this being for the drive mechanism including the tension line and part of the carriage, that will extend through this opening whenever the carriage is at one or the other extreme end of the machine. The carriage and attached cutting blade are indicated in the drawing at 18 and 36.

Other details and preferred construction of the assembly are shown with reference to the detailed drawings shown below.

FIG. 5 shows in perspective a portion of an end frame member 46 wherein the lower part of the end frame forms an opening 58, preferably rectangular, to accommodate the movement of the carriage to the extreme end of the machine. The wall panel opening 56a shown in the wall panel 56 is aligned with this rectangular frame opening 58. A limit switch 60 is retained in position adjacent to this opening 58, the limit switch having the purpose of stopping the motor driving up the tension cable that moves the carriage 18, when the carriage has reached the end of the machine. A limit switch finger or feeler 62 is contacted by the carriage, causing a signal to be sent from the limit switch 60 to the motor controls. In the embodiment shown, the limit switch is mounted against the side of the frame just above the opening 58, and retained therein by a limit switch cover 64 that can be an L-shaped metal cover as indicated. The cover can be bolted into the frame via holes 66 through the cover as shown, to engage with tapped holes in the frame member. Two of these limit switch assemblies are provided, one at each end of the machine.

FIG. 6 shows one of the cross beams 50. These cross beams are secured to the side frame members 44, as indicated in FIG. 4, using brackets 68, secured by welding or bolts. Each bracket 68 has bolt holes 70 for securement to the respective part of the side frame member. At the extreme ends of the frame these cross beams, because of other connections being made, may have different types of brackets. This is indicated in FIG. 4.

An important feature is shown in FIG. 6 and also FIG. 7. The cross beams have a feature that retains the grates in proper and accurate positioning within the frame. Formed or secured on the top of the cross beam at the center are grate stops 72, which may also be called grate locators or bumps or locator protrusions. The grates are formed of welded-together flat bars in vertical orientation, as can be seen in FIG. 8, for example. The flat bars at the corners of a grate, the side to be positioned toward the center of the machine, are placed on the cross beam so as to fit down into a gap 74 between a center locator or protrusion 72*a* and an adjacent side locator or protrusion 72*b*. It is the corner of the grate that engages the grate locators; each grate also extends around one of the side protrusions 72*b*, such that two 90°-angled flat bars of the grate engage over a side protrusion 72*b*, as best envisioned from the fragmentary section of cross beams 50 shown in FIG. 7. At the opposite end of the length of the grate, an opposing corner is engaged similarly with the bumps or grate locators 72, so that the grate is accurately located in the proper position.

FIG. 8 shows one of the grates 24. The inner side of the grate, i.e. the side toward the center of the machine, is at 24*b*, and the two corners on that side are those which will engage with the grate bumps or locators 72 as explained above. The outer side 24*c* of the grate sits adjacent to the side frame members as shown in FIGS. 3 and 4, and is different from the inner side in that a flat horizontal longitudinal rail 78 is included, as a surface for sliding engagement by a component of the cutting blade, as seen below. This skid plate surface and the outermost flat bar of the grate are preferably formed integrally, as a structural angle member 80 welded onto the adjacent flat bars. One leg of the angle member is the skid plate or longitudinal rail 78, while the other is seen at 82 as the last lengthwise flat bar of the grid.

The grate 24, which is primarily open as shown, preferably has dimensions of approximately two and a half feet by five feet, for a preferred embodiment wherein the width of the machine is about five feet. The openings can be about two inches by four inches and as such, compost material initially loaded into the machine will essentially not fall through the grates.

FIG. 9 shows the grate in top plan view, showing the skid plate or flat horizontal rail 78 at the outer side of the grate. The grate is shown broken and shortened, only the longitudinal ends being shown.

Figure 10:
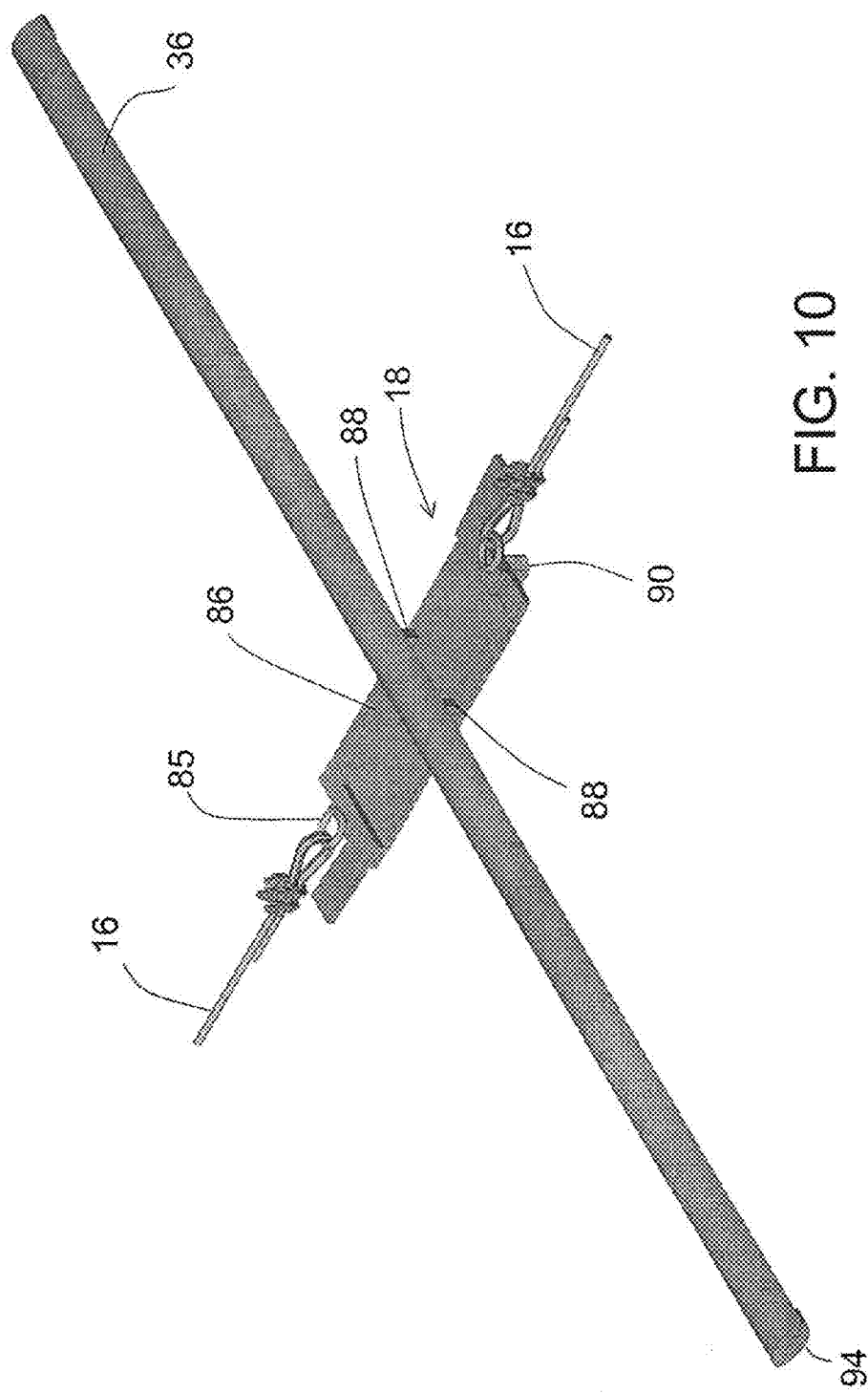
FIG. 10 is a perspective view showing a compost cutting blade of the machine, mounted on a movable carriage which is moved by tension cables.
Figure 11:
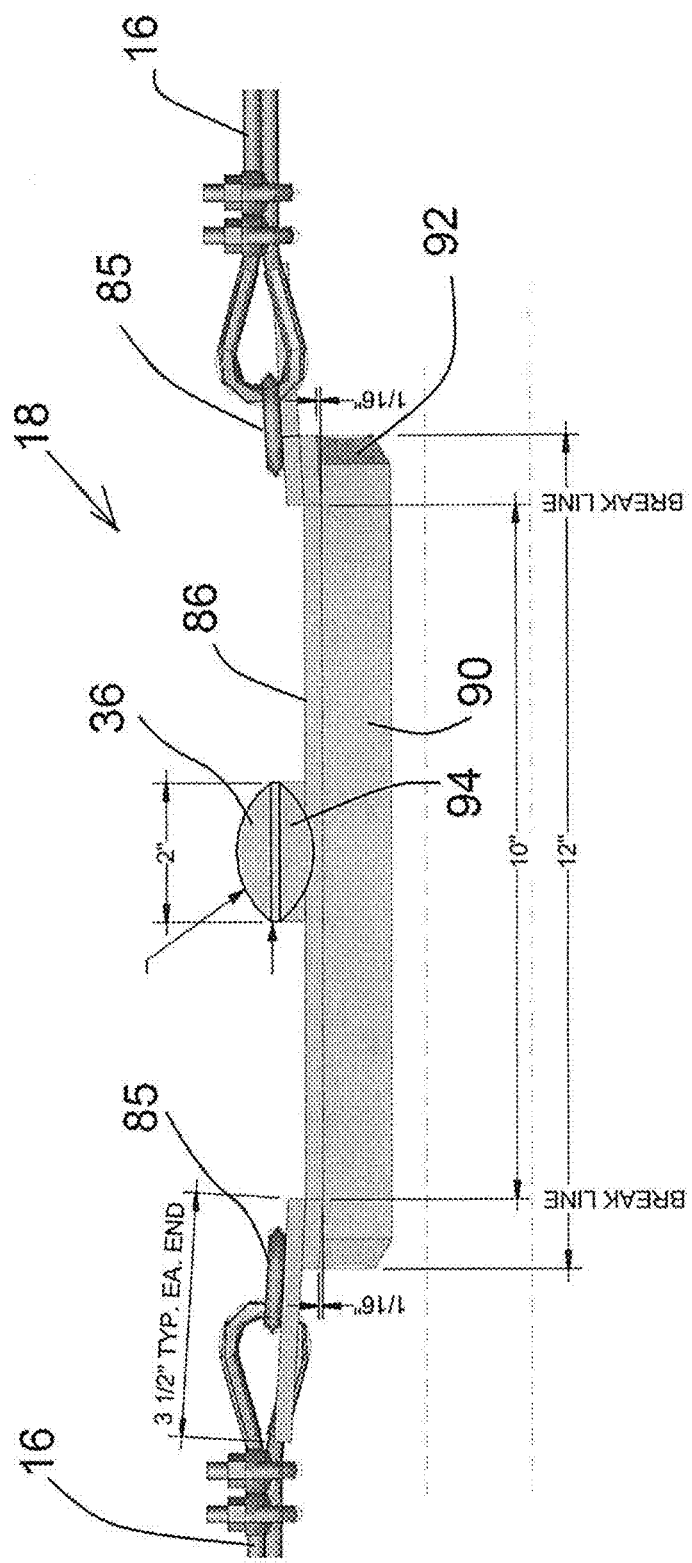
FIG. 11 is a side view showing the carriage and cutting blade.
Figure 12:
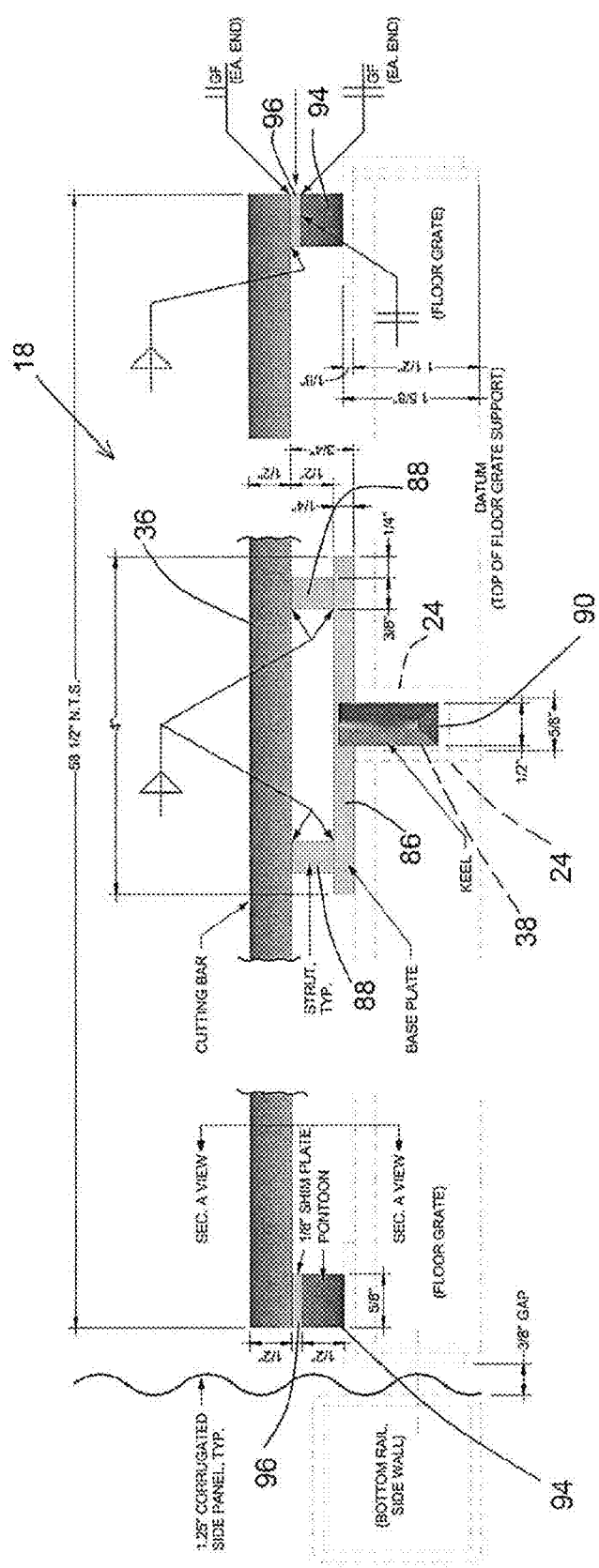
FIG. 12 is an end view relative to the machine, again showing the cutting blade and carriage.

FIGS. 10-12 show construction of the movable carriage assembly with the cutting blade. The carriage assembly, shown at 18, is provided with longitudinally fore and aft rings 85 secured to a metal base plate 86 by welding. These rings could be replaced by adequately reinforced holes through the plate itself. The ends of the tension cable 16 are secured to fore and aft ends of the carriage via the rings 85 (the carriage is sometimes referred to as having cables secured to it, at each of fore and aft ends). The cutting blade 36, preferably with a convex upper surface as shown, is retained above the compost floor (i.e. the tops of the grates) by a prescribed distance, with spacers 88 between the cutting blade and the base plate 86. A keel 90 is barely visible in FIG. 10, being a guiding element to ride in a track or channel 38 formed by the grates (FIG. 2), this keel being secured to the bottom side of the base plate 86. The keel 90 is better seen in FIGS. 11 and 12. The keel is short in length as compared to the transverse length of the cutting blade, which is typically about five feet. The keel preferably is no more than about fifteen inches in length, and more preferably, no more than about twelve inches in length. The keel is thus a quite short guiding element for a cutting blade which is about five feet in length (width with respect to the elongated machine); however, the grates provide a smooth central channel 38 through which the keel glides, so that a keel of only twelve inch length is sufficient. As noted above, the short length of the keel is important because a portion of the carriage with the keel must project out beyond the compost-containing area of the machine at the end of travel, and a much longer keel would cause the frame extensions 12 and 14, for the motor, gearbox and cable tensioner, to extend out farther. As shown, the keel has chamfered ends 92 as shown, to properly glide through the channel 38 formed between the grates, deflecting any edges of grates that might slightly protrude as the carriage advances.

FIGS. 10-12 show that the cutting blade or cutting bar 18 preferably carries spacers or "pontoons" 94 extending down to make contact with the skid plate surface 78 at outer sides of the grates as shown in FIGS. 8 and 9. These spacers or pontoons 94, which can include a shim plate 96 to achieve the proper spacing of the cutting blade ends above the compost floor, preferably are welded onto the flat bottom side of the cutting blade at the two outer ends, as shown.

FIG. 12 actually shows the keel 90 of the carriage residing in the glide channel 38 formed between the grates along a center line of the machine, the grates 24 being indicated in dashed lines.

Figure 13:
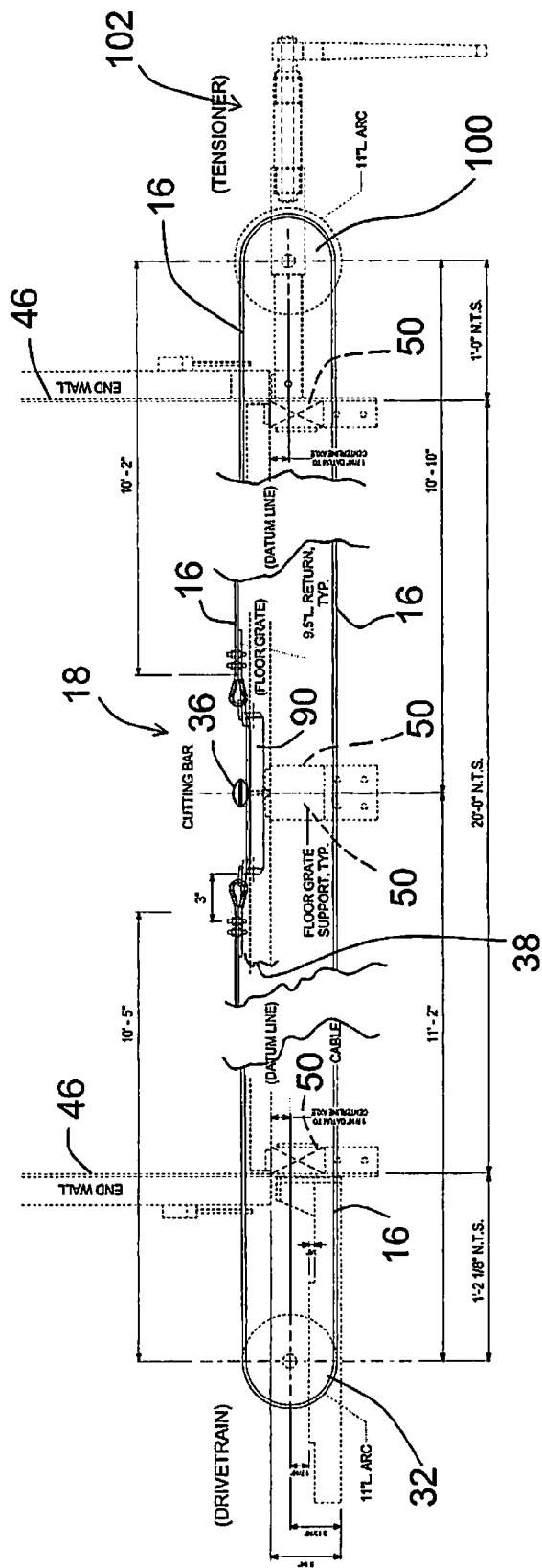
FIG. 13 is a schematic side elevation view showing the cable drive system of the invention.

In FIG. 13 the two end walls of the machine as defined by the end frame members 46 are indicated. FIG. 13 shows the drive pulley 32 at the motor end of the machine, the cable 16 riding over this pulley and over an opposite end pulley 100 that serves as a tensioner pulley, with indication of a tensioner assembly 102 for adjusting the position of the pulley 100 to adjust tension in the cable (explained further below), and showing the carriage 18 secured to the two ends of the tension cable 16. The drawing also indicates in dashed lines the guiding channel 38 formed by the space between left and right series of floor grates, and within which the keel 90 glides. As the carriage reaches either of the extreme ends of the machine, a portion of the carriage must extend beyond the end wall (identified as 46) so that the cutting blade can cut through the entire mass of compost. This dictates the outboard positions of the drive pulley 32 and of the tensioning pulley 100, and it is desirable to minimize the outboard distance of these elements, and thus the size of the frame extensions 12 and 14, as explained above. This is the primary advantage of the shorter keel 90.

Figure 14:
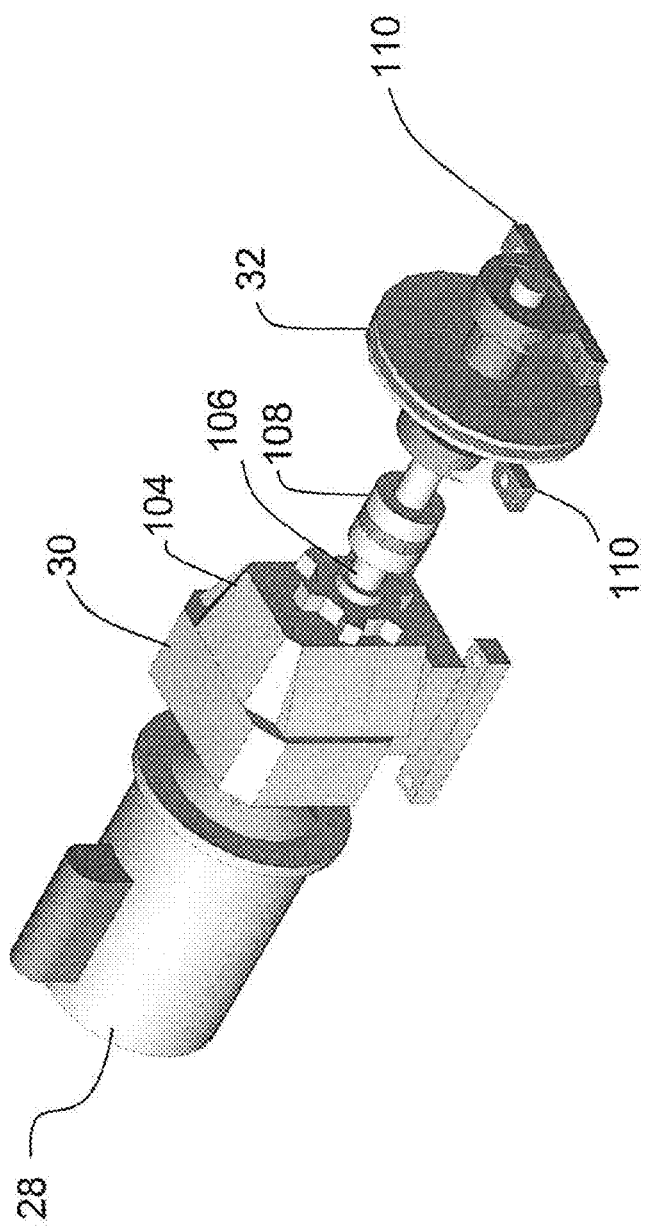
FIG. 14 is a perspective view indicating the motor, gearbox, a release coupler and a drive pulley of the machine.

FIG. 14 shows the motor 28, the gearbox 30 secured to a base mount 104 and a gear-reduced output drive shaft 106 leading to the drive pulley 32, with a overload release coupling 108 interposed in the shaft. The release coupling 108, which can be of the type known as a "Lovejoy", will break the drive connection to the pulley 32 in the event of excessive tension in moving the carriage. The release coupling can be selected to release at a torque level that will prevent damage to the motor, corresponding to any binding event that might occur with the cutting blade during its travel. Bearings supporting the drive pulley 32 are shown at 110, and these as well as the motor/gearbox are secured to the base plate 40 shown in FIG. 4, as well as in FIG. 15.

Figure 15:
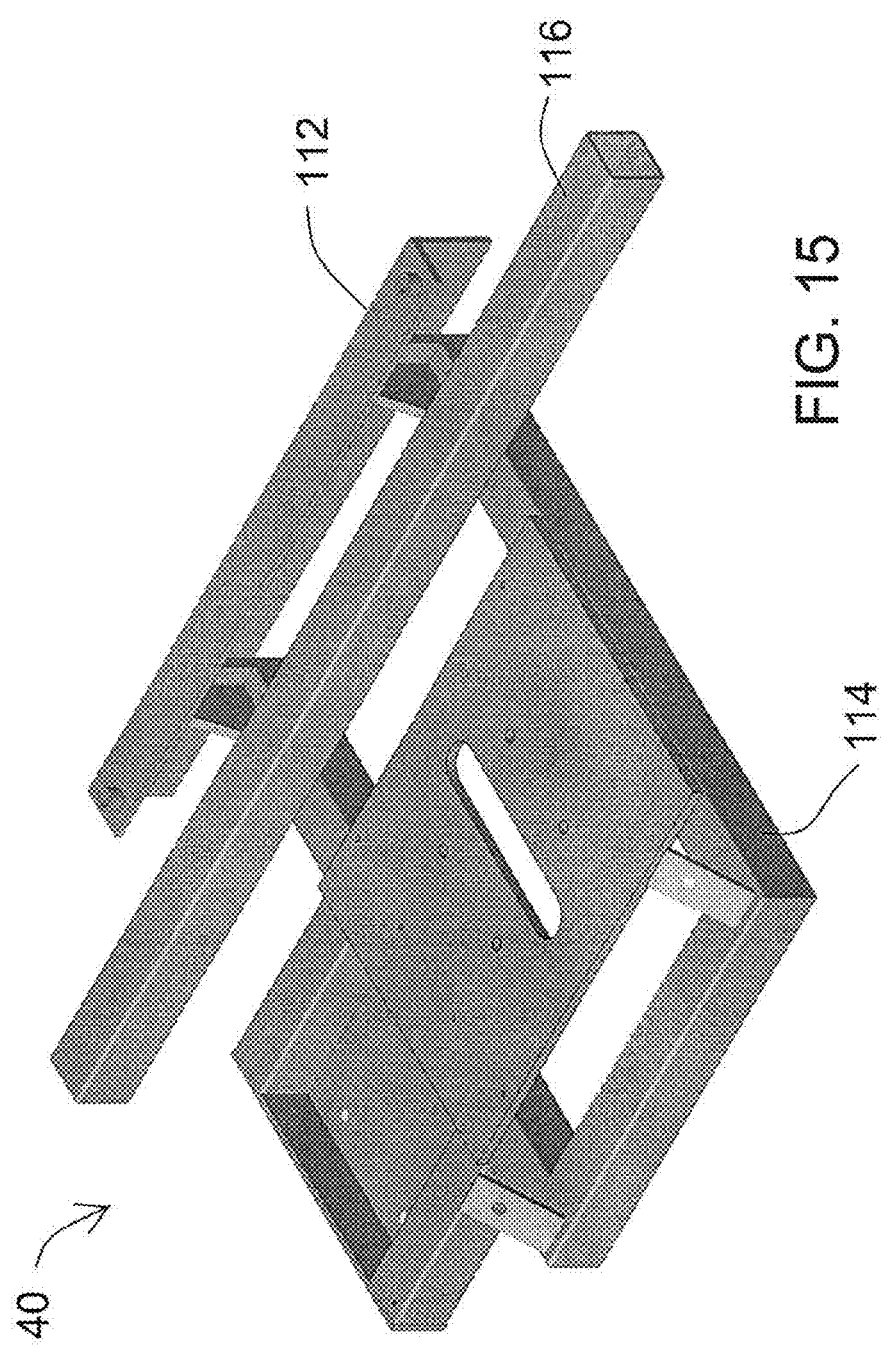
FIG. 15 is a perspective view showing a motor frame assembly on which the motor and gearbox of the machine are mounted.

FIG. 15 shows the base plate 40 in greater detail. The base plate is supported by a frame that includes a mounting angle 112 secured to a U-shaped base plate frame 114. A tube 116 is retained on the frame as a conduit channel for wiring the motor to a control panel, not shown.

Figure 16:
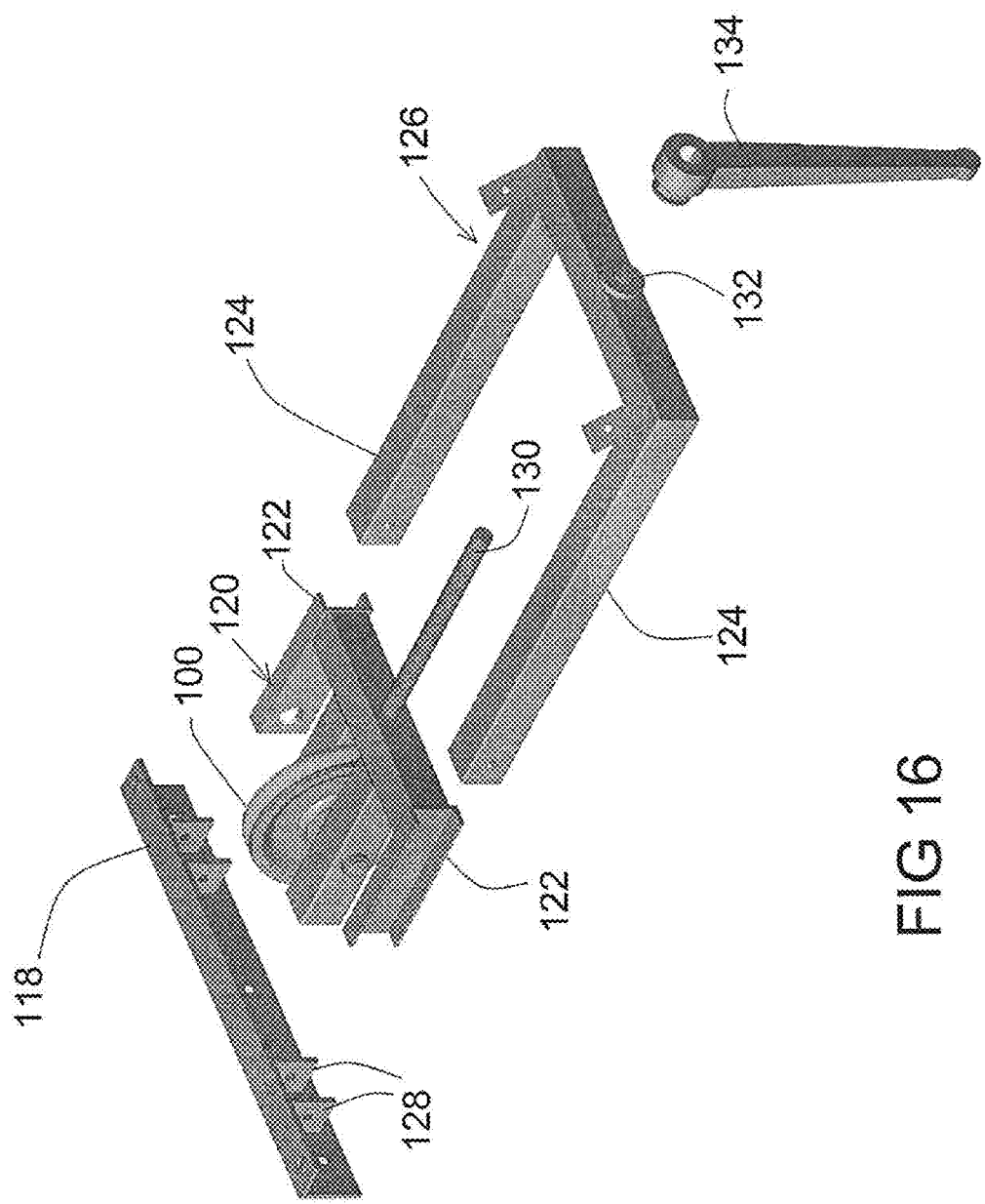
FIG. 16 is an exploded view in perspective, showing a cable tensioner of the machine.

FIG. 16 shows the cable tensioner, in exploded view. A mounting angle 118 provides for securing the system to the frame at the end of the machine. The tensioning pulley 100 mounted for rotation in a movable pulley frame 120 having side channels 122 that fit over box beams 124 of a U-shaped tensioner frame 126 that is secured to the mounting angle 118 via brackets 128. A threaded rod 130 is fixed to the pulley frame 120 and extends back as shown, to be positioned through a hole 132 at the back of the tensioner frame and engage with a threaded tensioner crank handle 134, preferably including a ratchet. The rotation of the crank handle 134, in a direction that advances the threaded rod 130 through the handle, will pull the pulley frame 120 in a direction to more tension in the cable riding over the pulley 100 (i.e. the direction to the right as seen in FIG. 16).

It is to be understood that although the above-described carriage driving system with motor-driven pulley and tension line is preferred, the carriage could be driven otherwise. Tension lines extending from each end of the carriage could be drawn in (and paid out) by a take-up reel or winch (not shown) at each end of the machine. The motor could drive one or more pumps to hydraulically take up the cables at either end for back and forth carriage movement, as one example.

The operation of the composting system of the invention is described above. Preferably the machine is used in conjunction with a precomposting step, in another machine or simply in a compost pile. Compost material such as manure is composted for approximately two weeks, then loaded into the machine.

Assuming the machine already contains composting material, the precomposted material is added at the top of the mass compost of the machine, and it is added periodically, to balance harvest of finished compost from the bottom of the machine. As noted above, a better quality compost is achieved using worms, producing "vermicompost". If a compost mass is already existent in the machine, it will contain approximately 400 pounds of worms in a forty foot system, or approximately two pounds of worms per square foot of compost floor area. If the addition of compost is an initial loading of a machine, then the worms must be added.

In the composting machine the compost mass is typically about 20 inches to 24 inches in depth. The vermicomposting process typically requires about 60 days retention time in the machine, from the point a new batch of precompost is added to the top of the compost mass, to the point where the vermicompost product of that particular material is harvested. A forty foot machine in accordance with the invention as described above, with about five foot width, can typically yield about twenty-five yards of finished vermicompost per year, the finished product being produced from about twice that volume of precompost loaded into the machine. Since precomposting also reduces the volume of the compost material, the finished vermicompost might typically be about 40% down to 25% of the volume of the original material prior to precomposting.

The above figures are approximate and assume the compost material is manure. Many typical sources of manure, as from dairy farms, contain rice hulls with the manure. Rice hulls are often used in bedding for the animals. The rice hulls improve the carbon-nitrogen ratio for composting (a good ratio is about 30:1).

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A worm composting machine, comprising:
    an elongated support frame, at least about fifteen feet in length and with a width dimension much smaller than the length;
    a series of cross beams in the support frame extending transversely, the support frame including side and end frame members, side walls and end walls connected to the side and end frame members;
    a series of grates resting horizontally on the support frame above the cross beams, the grates being primarily open and positioned on the support frame in series with a longitudinal gap formed between the edges of the grates along a longitudinal center line of the frame, the longitudinal gap forming a guide channel continuous through the length of the series of grates, and the grates forming a compost-supporting floor;
    a carriage movable along the frame through the length of the series of grates, the carriage having two opposed longitudinal ends and having a keel slidably positioned within the guide channel, the keel having a length no greater than about 15 inches and the carriage further includes a compost cutting blade extending transversely across the width of the series of grates and spaced above the grates by a selected distance; and
    a carriage driving mechanism including a tension line connected to each of the two opposed longitudinal ends and extending from the carriage in each of two opposed longitudinal directions, and a motor and drive system driving the tension line, with a motor control for causing the carriage to be moved from one end of the machine to the opposite end, drawing the cutting blade from one end of the series of grates to the opposite end, cutting a bottom layer of compost of a desired thickness and discharging the compost having said desired thickness down through the series of grates.

2. The composting machine of claim 1, wherein the keel has a length no greater than about 12 inches.

3. The composting machine of claim 1, wherein the cutting blade has a cross-sectional shape convexly curved at an upper side.

4. The composting machine of claim 3, wherein the cutting blade is planar at a lower side, and the ends of the cutting blade each having a spacer extending down from the lower side of the blade and positioned to rest on and slide on the grates to maintain the ends of the cutting blade spaced above the grates by said selected distance.

5. The composting machine of claim 4, wherein outer sides of the series of grates include a flat horizontal longitudinal rail on which the spacers of the cutting blade rest.

6. The composting machine of claim 1, wherein the support frame has a length at least about twenty feet.

7. The composting machine of claim 1, wherein the support frame has a length at least about forty feet.

8. The composting machine of claim 1, wherein the cross beams include raised locator protrusions at upper sides of the cross beams, the protrusions extending up into openings of the grates for properly locating the grates in the frame.

9. The composting machine of claim 1, further including a frame extension at one end of the support frame, supporting the motor at said one end.

10. The composting machine of claim 9, further including a second frame extension at an opposite end of the frame, with a tensioner supported on the second frame extension and connected to the tension line, with means for adjusting the tension in the tension line.

11. The composting machine of claim 1, further including a gear box connected to and driven by the motor, and a pulley driven by the gear box, the tension line extending around the pulley.

12. The composting machine of claim 11, further including an adjustable tensioner connected to the tension line.

13. The composting machine of claim 1, further including a release coupling in the drive system, disengaging the drive system if a preselected load occurs during movement of the carriage by the drive system.

14. A Composting system comprising the worm composting machine of claim 1 and a compost pile with live worms therein, wherein the compost pile is at least about 24 inches deep, and positioned within the worm composting machine.

15. The composting machine of claim 1, wherein said selected distance is about ¾".

\* \* \* \* \*